US00PP21183P3

(12) United States Plant Patent
Blom

(10) Patent No.: US PP21,183 P3
(45) Date of Patent: Aug. 3, 2010

(54) ***CHRYSANTHEMUM* PLANT NAMED 'ZANMUTOMIC'**

(50) Latin Name: *Chrysanthemum×morifolium Ramat.*
Varietal Denomination: Zanmutomic

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/314,960

(22) Filed: Dec. 19, 2008

(65) Prior Publication Data

US 2010/0162455 P1 Jun. 24, 2010

(51) Int. Cl.
*A01H 5/00* (2006.01)

(52) U.S. Cl. ..... Plt./290

(58) Field of Classification Search ..... Plt./290
See application file for complete search history.

*Primary Examiner*—Kent L Bell
(74) *Attorney, Agent, or Firm*—Steptoe & Johnson LLP

(57) ABSTRACT

A *chrysanthemum* plant named 'Zanmutomic' characterized by its medium sized blooms with bronze ray florets and prolific branching; natural season flower date September 814 13; blooming for a period of 5 weeks.

3 Drawing Sheets

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmutomic'. 'Zanmutomic' is a product of a breeding and selection program for outdoor pot mums (garden mums) which had the objective of creating new *chrysanthemum* cultivars with a double type inflorescence, a natural season flower date starting at September 8–13, blooming for a period of 5 weeks. 'Zanmutomic' is a seedling resulting from the crossing of the female parent id 2863 and male parent id 3393. Plants of 'Zanmutomic' differ from plants of the female parent in growth habit, that of the seedling is more ball shaped. Plants of 'Zanmutomic' differ from plants of the male parent in the following characteristics. (1) earlier blooming period of seedling (2) less vigor in seedling.

The new and distinct cultivar was discovered and selected as a flowering plant by Wilhelmus Bernardus Blom on a cultivated field in Rijsenhout, The Netherlands in 2005. The first act of asexual production of 'Zanmutomic' was accomplished when vegetative cuttings were used from the initial selection in 2005 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
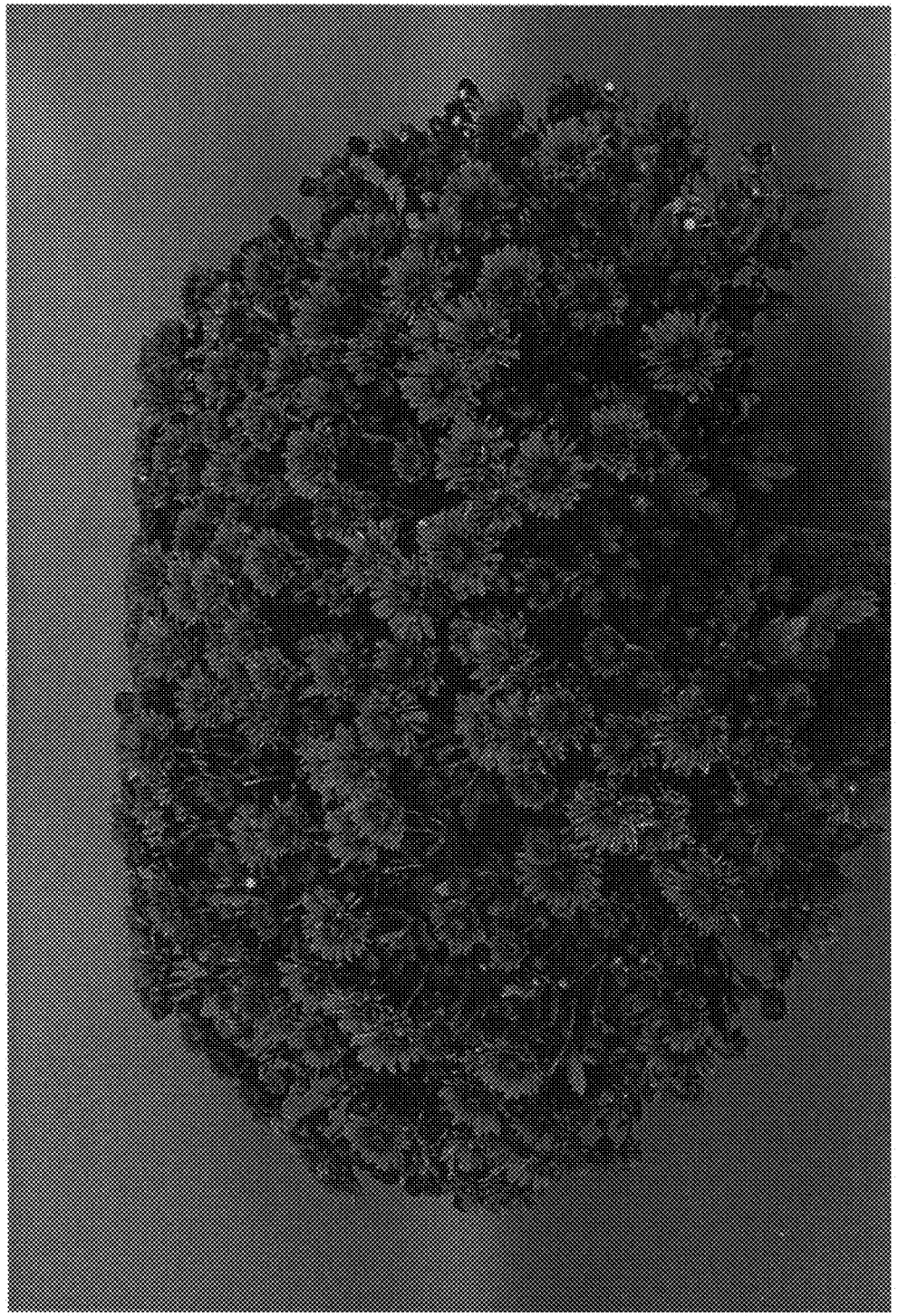
FIG. 1 shows a plant of the cultivar in full bloom.
Figure 2:
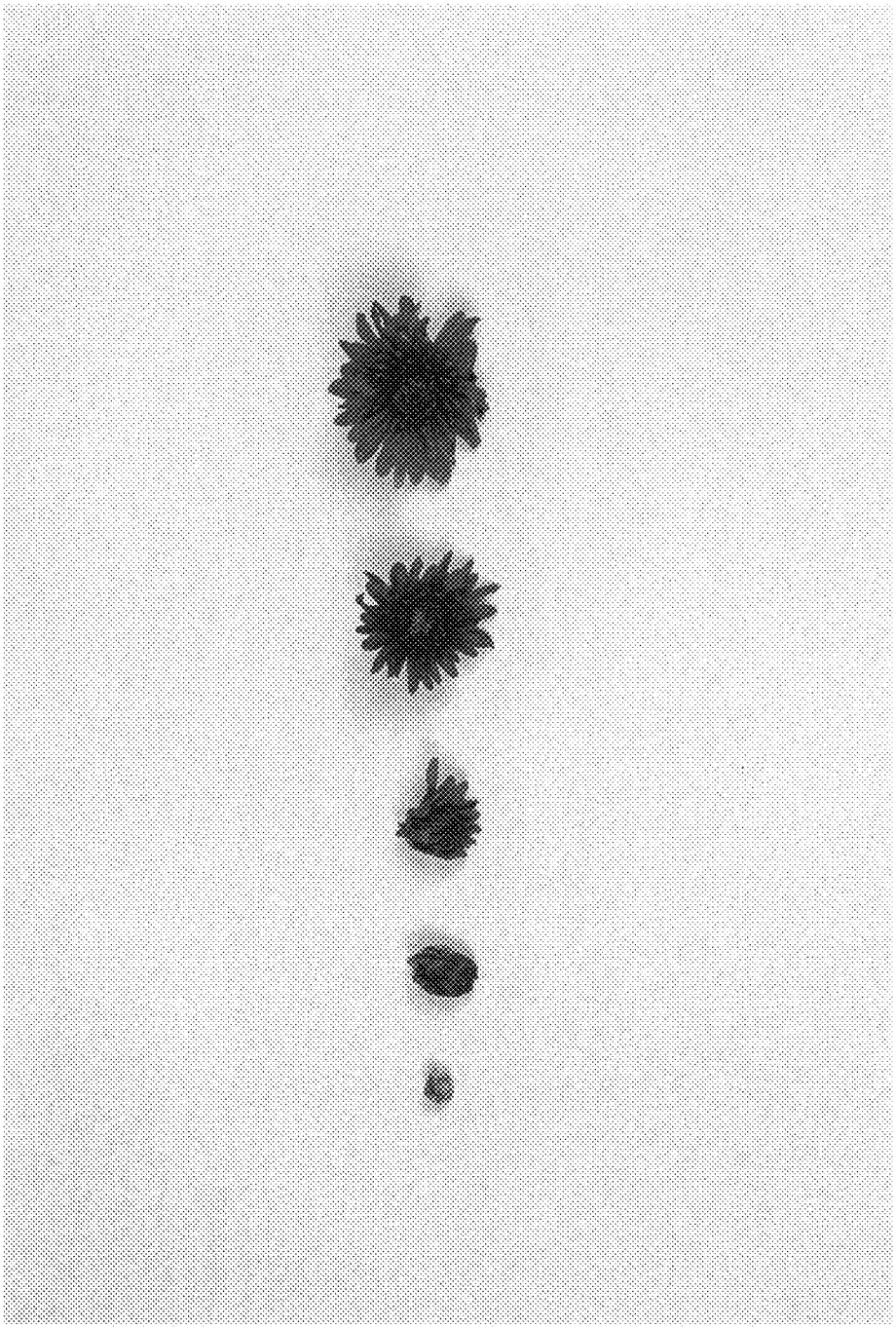
FIG. 2 shows the various stages of bloom of the new cultivar.
Figure 3:
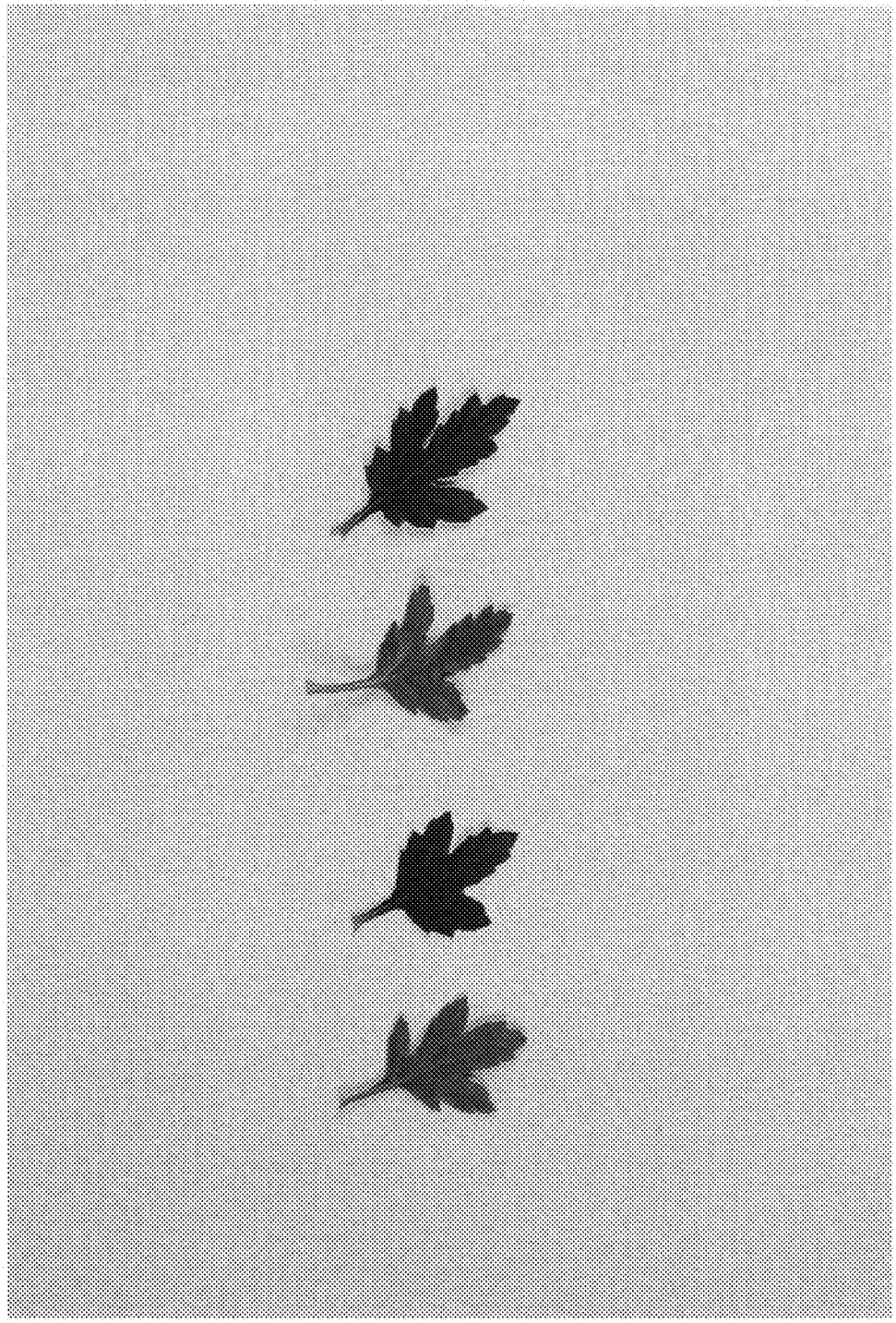
FIG. 3 shows the various stages of foliage of the new cultivar.

The observations and measurements were gathered from plants grown out door in Rijsenhout, The Netherlands under natural day length and temperature and planted in week 22 in 2008. The natural blooming date of this crop was September 8–13. The average height of the plants was 25 cm. No growth retardants were used. No tests were done on disease or insect resistance or susceptibility. No tests were done on cold or drought tolerance. This new variety produces medium sized blooms with bronze ray florets blooming for a period of 5 weeks.

From the cultivars known to inventor the most similar existing cultivar in comparison to 'Zanmutomic' is 'Zanmusunset' (U.S. Plant Pat. No. 20,475). When 'Zanmusunset' and 'Zanmutomic' are being compared the following differences are noticed: The differences of 'Zanmusunset' and 'Zanmutomic' are (1) Number of ray-florets. And (2) Plant size. (1) The number of ray-florets in 'Zanmusunset' is higher than in those of 'Zanmutomic'. (2) The plants of 'Zanmusunset' are larger in size than those of 'Zanmutomic'. The following is a description of the plant and characteristics that distinguish 'Zanmutomic' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical description of *Chrysanthemum* x*morifolium* Ramat. 'Zanmutomic'

| | |
|---|---|
| Bud | |
| Size | Small; cross-section 0.5-0.7 cm, height 0.5 cm |
| Shape | Oblate |

TABLE 1-continued

Botanical description of *Chrysanthemum* x*morifolium* Ramat. 'Zanmutomic'

| | |
|---|---|
| Texture | Pubescent |
| Outside Color | Greyed-green 191A |
| Phyllaries | |
| Number | 22-24, arranged in 3 rows |
| Shape | Elliptic |
| Apex | Acute |
| Base | Truncate |
| Margin | Entire |
| Color | Upper surface: Greyed-green 191A<br>Lower surface: Greyed-green 191C |
| Length and width | 5-7 mm; 2 mm |
| Texture | Pubescent |
| Inflorescence | |
| Type | Double |
| Height | 2 cm |
| Diameter | 5 cm |
| Peduncle length | 8 cm |
| Peduncle color | Green N138C |
| Peduncle diameter | 1 mm |
| Peduncle surface | Pubescent |
| Number per branch | Approx. 7-9 inflorescences |
| Flowering period individual bloom | Ca. 4 weeks |
| Seeds | Produced in small quantities, ovate, Greyed-brown 199A, length 1.5 mm, diameter 0.8 mm |
| Fragrance | Faint *chrysanthemum* odor |
| Color | |
| Center of inflorescence | Immature stage: Greyed-orange 172A<br>Mature stage: Yellow-orange 21C |
| Color of upper surface of the ray-florets | Greyed-orange 172A |
| Color of the lower surface of the ray-florets | Greyed-orange 167C |
| Tonality from Distance | A garden mum with bronze inflorescences |
| Color of the ray-florets after aging of the plant | Greyed-orange 171D |
| Ray florets | |
| Texture | Upper and lower side smooth |
| Number | Ca. 130 |
| Shape | Elliptic |
| Apex | Rounded |
| Base | Attenuate |
| Cross-section | Flat |
| Longitudinal axis of majority | Straight |
| Length of corolla tube | 3 mm |
| Ray-floret margin | Entire |
| Ray-floret length | 2-3 cm |
| Ray-floret width | 3-5 mm |
| Ratio length/width | High |
| Disc florets | |
| Disc diameter | 2 mm |
| Number | Ca. 5 (only visible in mature inflorescences) |
| Shape | Tubular |
| Color | Yellow 11D at apex; Yellow green 150D at base |
| Length | Ca. 0.5 mm |
| Diameter | Ca. 0.3 mm |
| Receptacle | |
| Color | Green 138D |
| Shape | Conical raised |
| Height | 4 mm |
| Diameter | 3 mm |

TABLE 1-continued

Botanical description of *Chrysanthemum* x*morifolium* Ramat. 'Zanmutomic'

| | |
|---|---|
| Reproductive Organs | |
| Androecium | Present in disc florets only |
| Stamen length | 3 mm |
| Stamen color | Yellow-green 144A |
| Anther color | Yellow 3A |
| Pollen | Scarce |
| Pollen | Yellow 12A |
| Gynoecium | Present in both ray and disc florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Grown as a potmum, outdoor raised and mounded |
| Growth habit | Spherical shape |
| Growth rate | Medium |
| Height | 25 cm |
| Width | 45 cm |
| Stem Color | Greyed-brown 199A |
| Stem Strength | Strong |
| Stem Brittleness | Not brittle |
| Stem Anthocyanin Coloration | Not observed |
| Internode length | 5-10 mm |
| Length of lateral branch | From top to bottom 20-22 cm |
| Lateral branch color | Green 137 C |
| Lateral branch brittleness | Medium |
| Lateral branch diameter | 2 mm |
| Branching (average number of lateral branches) | Prolific with 9 breaks after pinching |
| Natural season blooming date | September 8-13 to October 13-18 |
| Foliage | |
| Leaf color | Upper side: Green 139A to 139B<br>Lower side: Green 138B |
| Color midvein | Upper side: Yellow-green 147D<br>Lower side: Yellow-green 148D |
| Size | Small.; length 4-5 cm, width 2.5-3 cm |
| Quantity (number per lateral branch) | 28-30 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronulate |
| Petiole length | 1.5-2 cm |
| Petiole diameter | 2 mm |
| Petiole color | Yellow-green 147D |

TABLE 2

Differences with the comparison variety

| | 'Zanmutomic' | 'Zanmusunset' |
|---|---|---|
| Number of ray-florets | Ca. 130 | 220-230 |
| Plant height | 25 cm | 40-45 cm |
| Plant width | 45 cm | 55 cm |

I claim:

1. A new and distinct variety of *chrysanthemum* plant as described and illustrated.

* * * * *